US010610252B2

(12) United States Patent
Marchand (10) Patent No.: US 10,610,252 B2
(45) Date of Patent: Apr. 7, 2020

(54) NON-MORCELLATING MINIMALLY INVASIVE SURGICAL TISSUE REMOVAL SYSTEM (71) Applicant: Greg Marchand, Mesa, AZ (US)

(72) Inventor: Greg Marchand, Mesa, AZ (US)

(73) Assignee: Marchand Institute for Minimally Invasive Surgery, Mesa, AZ (US)

( * ) Notice: Subject to any disclaimer, the term of this patent is extended or adjusted under 35 U.S.C. 154(b) by 64 days.

(21) Appl. No.: 15/862,349

(22) Filed: Jan. 4, 2018

(65) Prior Publication Data
US 2019/0201032 A1 Jul. 4, 2019

(51) Int. Cl.
A61B 17/32 (2006.01)
A61B 17/34 (2006.01)
A61B 17/00 (2006.01)
A61B 17/42 (2006.01)

(52) U.S. Cl.
CPC .. *A61B 17/32002* (2013.01); *A61B 17/00234* (2013.01); *A61B 17/3423* (2013.01); *A61B 2017/00287* (2013.01); *A61B 2017/32006* (2013.01); *A61B 2017/320024* (2013.01); *A61B 2017/3466* (2013.01); *A61B 2017/4216* (2013.01)

(58) Field of Classification Search
CPC ........ A61B 17/32002; A61B 17/00234; A61B 17/3423; A61B 2017/00287; A61B 2017/320024; A61B 2017/32006; A61B 2017/3466; A61B 2017/4216; A61B 2017/0029; A61B 2017/00336
See application file for complete search history.

(56) References Cited

U.S. PATENT DOCUMENTS

| 5,788,709 | A | * | 8/1998 | Riek | A61B 17/00234 606/110 |
| 8,585,712 | B2 | * | 11/2013 | O'Prey | A61B 17/26 606/114 |
| 2014/0371760 | A1 | * | 12/2014 | Menn | A61B 17/00234 606/114 |
| 2015/0289864 | A1 | * | 10/2015 | Holsten | A61B 17/00234 606/114 |
| 2016/0262794 | A1 | * | 9/2016 | Wachli | A61B 17/3423 |
| 2018/0206831 | A1 | * | 7/2018 | Wyckoff | A61B 17/00234 |

* cited by examiner

Primary Examiner — Christopher R Harmon
(74) Attorney, Agent, or Firm — Michael D Lindsey (57) ABSTRACT

In the field of minimally invasive or laparoscopic surgery, in there exists several devices for the purposes of removing large tissues from the abdomen through the use of only small holes. All of these devices, to date, to the knowledge of the inventor have involved morcellation, or the breaking apart of these tissues into small pieces. The surgical device, through the use of a unique engulfing sheet or engulfing bag, has the capability of removing a tissue from the abdomen through small minimally invasive or laparoscopic incisions without the use of morcellation. The device relies upon mechanical energy to force a large object through a smaller hole without the necessity to break the object down into smaller pieces.

6 Claims, 5 Drawing Sheets

NON-MORCELLATING MINIMALLY INVASIVE SURGICAL TISSUE REMOVAL SYSTEM

BACKGROUND OF THE INVENTION

1. Field of the Invention

The present invention relates generally to medical instruments, and more specifically it relates to instruments related to laparoscopy and all surgery that is performed through tiny incisions.

2. Description of the Related Art

Any discussion of the prior art throughout the specification should in no way be considered as an admission that such prior art is widely known or forms part of common general knowledge in the field.

Medical instruments have been in use for years. Typically, medical instruments vary greatly in configuration depending on what procedure that the medical instruments are utilized.

One such procedure that medical instruments are utilized are minimally invasive or laparoscopic procedures.

During a minimally invasive or laparoscopic procedure a tissue removal system is generally utilized to remove any objects that are larger than the incisions that were made to enter the abdomen, such as but not limited to large uteri, large ovaries, sections of the bowel, primary abdominal tumors, and tumors of the pancreas, stomach, kidneys, ureters, adrenal glands, large and small bowel, vascular system, as well as pregnancies within the uterus and outside the uterus. The tissue removal system allows the surgeon to remove large masses of tissue without needing to make larger incisions. Generally tissue removal systems have included some form of morcellation, or breaking the tissue into pieces, in order to remove the tissue through the small holes. This breaking apart of tissue or morcellation has been described using round blades, straight blades, electrical energy, and other means.

To the knowledge of the inventor there has been no invention of a surgical tissue removal system utilizing mechanical energy to force a tissue through a small diameter incision or hole without first breaking the tissue into pieces or morcellating the tissue. The device described herein relies upon the strength and relative impenetrability of an engulfing bag, as well as the mechanical energy of an electric or manually powered device, to force a tissue mass through a strong, small diameter ring harness without first breaking the tissue mass into pieces. Such an invention, as described in this application, would eliminate the risks that are inherent to morcellation of tissue and accomplish the removal of a large tissue without the use of morcellation.

BRIEF SUMMARY OF THE INVENTION

In view of the foregoing disadvantages inherent in the known types of medical instruments now present in the prior art, the present invention provides a new minimally invasive or laparoscopic tissue removal system construction wherein the same can be utilized to remove large masses of tissue in the abdomen or pelvis without the risks inherent to morcellation, including spillage and seeding of malignant diseases. The general purpose of the present invention, which will be described subsequently in greater detail, is to provide a new minimally invasive or laparoscopic tissue removal system that has many of the advantages of the medical instruments mentioned heretofore and many novel features that result in a new minimally invasive or laparoscopic tissue removal system which is not anticipated, rendered obvious, suggested, or even implied by any of the prior art medical instruments, either alone or in any combination thereof. To attain this, the present invention generally comprises a largely impenetrable engulfing sheet or engulfing bag, which is then pulled through a ring harness using mechanical energy. The strength of the engulfing bag or sheet as well as the power of the mechanical device physically change the shape of the soft tissue mass contained therein, not unlike the squeezing of a common toothpaste tube make change the shape of the contained contents, forcing the contents out through a small, solid hole surrounded by a harness. The harness must be elevated a small distance above the level of the skin to avoid catching the skin in the working parts of the harness and associated mechanical apparatus. The engulfing bag or engulfing sheet may be square, square with extended "wing like corners," rounded, or may have a three dimensional "bag" shape to it. There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings.

The invention is capable of other embodiments and of being practiced and carried out in various ways. Also, it is to be understood that the phraseology and terminology employed herein are for the purpose of the description and should not be regarded as limiting.

A primary object of the present invention is to provide a minimally invasive or laparoscopic tissue removal system that will overcome the shortcomings of the prior art devices.

A second object is to provide a minimally invasive or laparoscopic tissue removal system for increasing the speed and efficiency of a minimally invasive or laparoscopic procedure.

Another object is to provide a minimally invasive or laparoscopic tissue removal system that decreases the need to enlarge incisions used to perform minimally invasive or laparoscopic surgery A further object is to decrease the risk of seeding a known or unknown cancer throughout the abdominal cavity or other body cavity, which is a risk inherent to removing any mass from the abdominal cavity or other body cavity at time of surgery. While previously described devices may be suitable for the particular purpose to which they address, they are not as suitable for performing the tissue removal without resorting to morcellation.

In these respects, the minimally invasive or laparoscopic tissue removal system according to the present invention substantially departs from the conventional concepts and designs of the prior art, and in so doing provides an apparatus primarily developed for the purpose of improving minimally invasive or laparoscopic tissue removal without resorting to morcellation or breaking a tissue into pieces.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview

Figure 1:
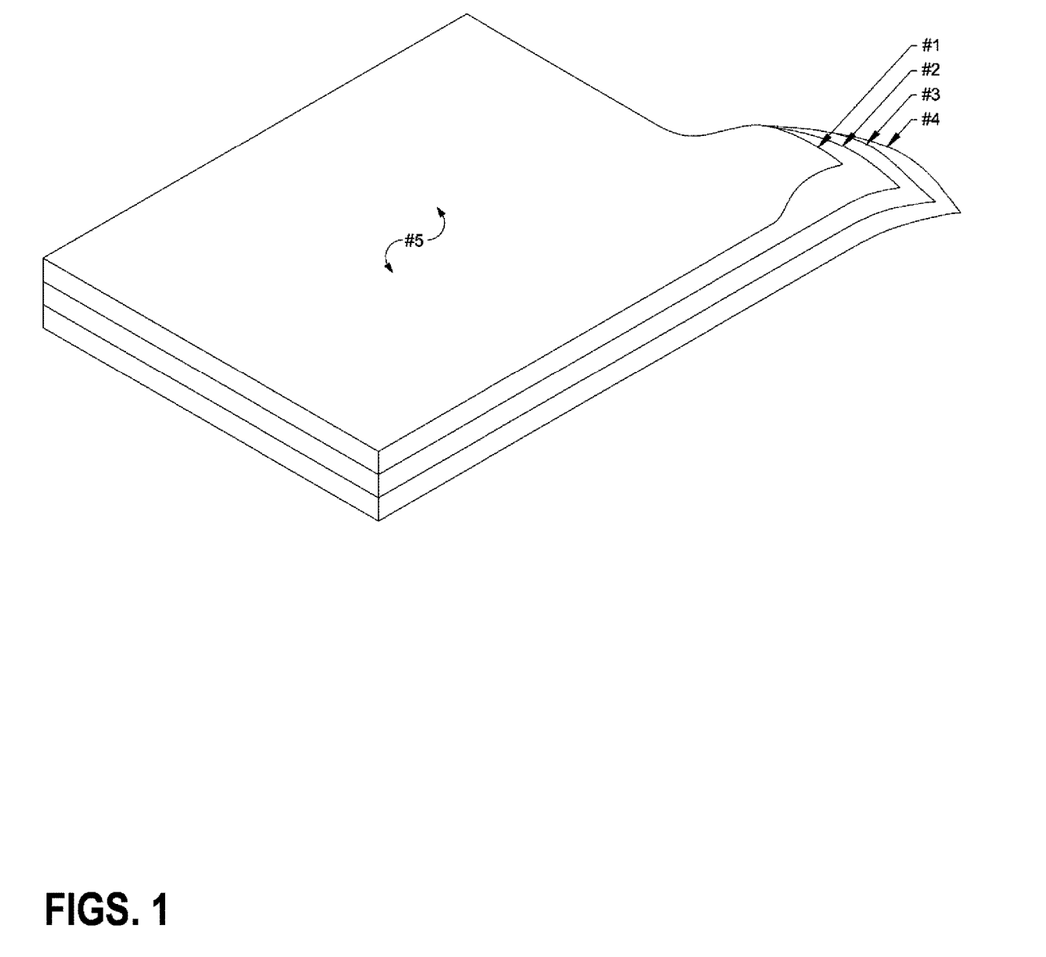
FIG. 1 is a side perspective view of the engulfing bag or engulfing sheet portion of the present invention. The engulfing bag or engulfing sheet is presented in a square shape in this representation.

Turning now descriptively to the drawings, in which similar reference characters denote similar elements throughout the several views, FIGS. 1 through 5 illustrate a minimally invasive or laparoscopic tissue removal system, which comprises a engulfing sheet or engulfing bag with or without a series of guiding tracks and a ring harness, through which the engulfing sheet or engulfing bag will be pulled, effectively reducing the diameter of the tissue within the engulfing mass to the diameter of the ring harness. The device also may include a deployment tube in order to enter the patient's body cavities as well as a collapsible stabilizing harness in order to force the engulfing sheet or engulfing bag around the tissue mass to be removed, thus encapsulating the mass in all directions except the mouth of the bag. This can be accomplished by placing the mass in the engulfing sheet or engulfing bag manually with another instrument or with a "scooping technique" using the weight of the mass to fall into the engulfing sheet or engulfing bag. The deployment tube and collapsible stabilizing harness may be made of metal, plastic, kevlar, or other materials. This could also be accomplished in some variations without the use of a deployment tube, collapsible stabilizing harness, or neither. As shown in FIG. 1, the described engulfing bag or engulfing sheet comprises of multiple layers of largely impenetrable materials. (#1, #2, #3, #4) These materials may include alternating or repeating layers of metal, plastic, rubber, kevlar, or other materials in order to achieve the goals of flexibility, strength, and to a reasonable degree having the characteristic of being impenetrable. These materials may be fashioned into sheets of mesh, chain like sheets, three-dimensional woven sheets, sheets of connected plates, or other configurations to achieve the goals of flexibility, strength, and to a reasonable degree having the characteristic of being impenetrable. The collapsible stabilizing harness and deployment tube are not visualized in FIG. 1.

Figure 2:
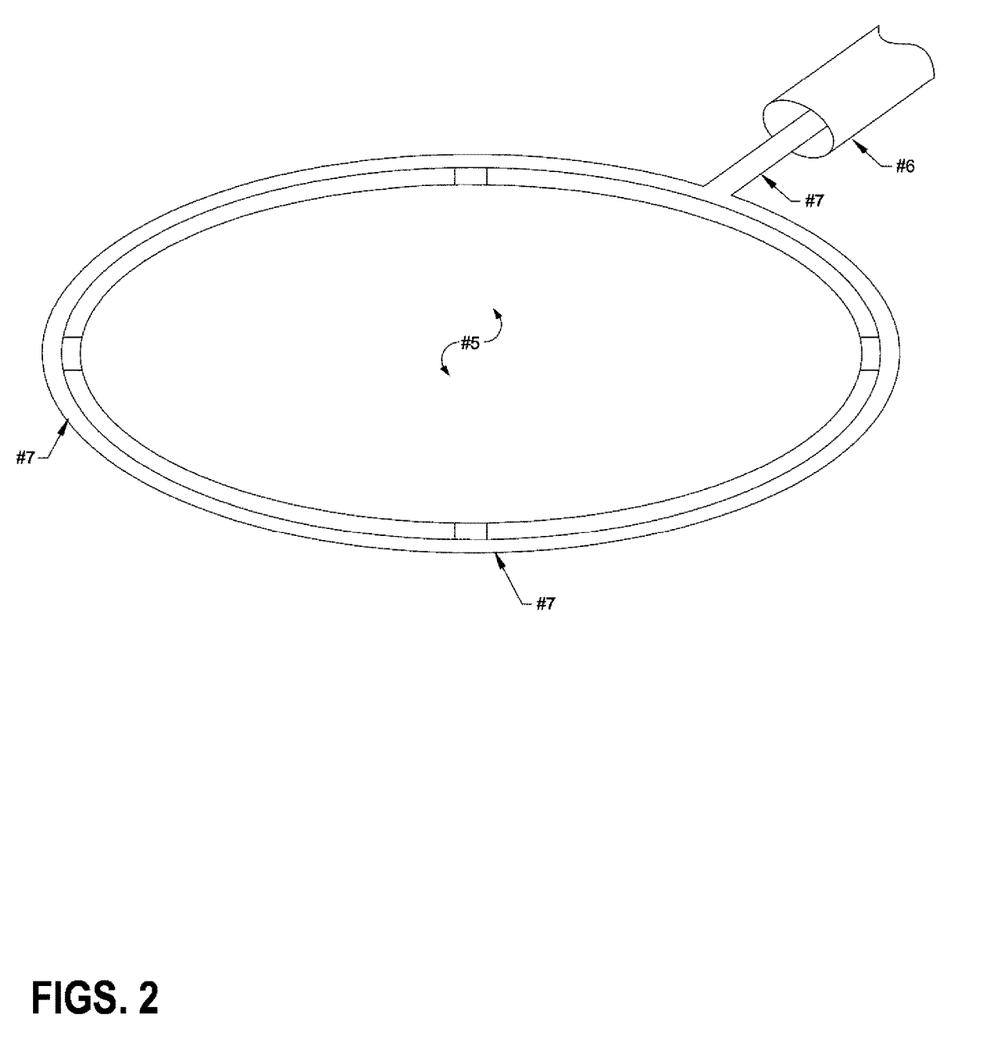
FIG. 2 is an above perspective view of the engulfing bag or engulfing sheet portion of the present invention. The engulfing bag or engulfing sheet is presented in a round shape in this representation, and is attached to the removable deployment tube and collapsible stabilizing harness.

As seen in FIG. 2, one side of the engulfing sheet or engulfing bag (#5) will directly interface with the tissue mass being removed. This side of the sheet may interface with the gears or rolling pins of the second inner ring harness shown in FIG. 4 in a configuration which utilizes a second inner ring harness (#13), and gears or rolling pins. The deployment tube (#6) is also show in FIG. 2. as it may serve to keep a small diameter to allow the engulfing sheet or engulfing bag, as well as the collapsible stabilizing harness (#7) to enter the patient's body, in order to engulf the tissue mass to be removed. The collapsible stabilizing harness must be flexible to enter through a small diameter and then expand to accommodate large tissue mass volumes. The collapsible stabilizing harness may constitute a full ring around the engulfing sheet or engulfing bag, or may border only a portion of the engulfing sheet or engulfing bag in other configurations. In this configuration the collapsible stabilizing harness is shown completely deployed (not collapsed) to illustrated that some degree of collapse will be necessary to fit the collapsible stabilizing harness into the much smaller diameter deployment tube. In the configuration shown in this figure the collapsible stabilizing harness is represented as a fully bordering the entire engulfing sheet or engulfing bag. In other configurations, the collapsible stabilizing harness may border only a portion of the engulfing sheet or engulfing bag. In this configuration the collapsible stabilizing harness is shown completely engaged to illustrated that some degree of collapse will be necessary to fit the collapsible stabilizing harness into the much smaller diameter deployment tube. The collapsible stabilizing harness may be permanently attached to the engulfing sheet or engulfing bag, or may be removable from the bag.

Figure 3:
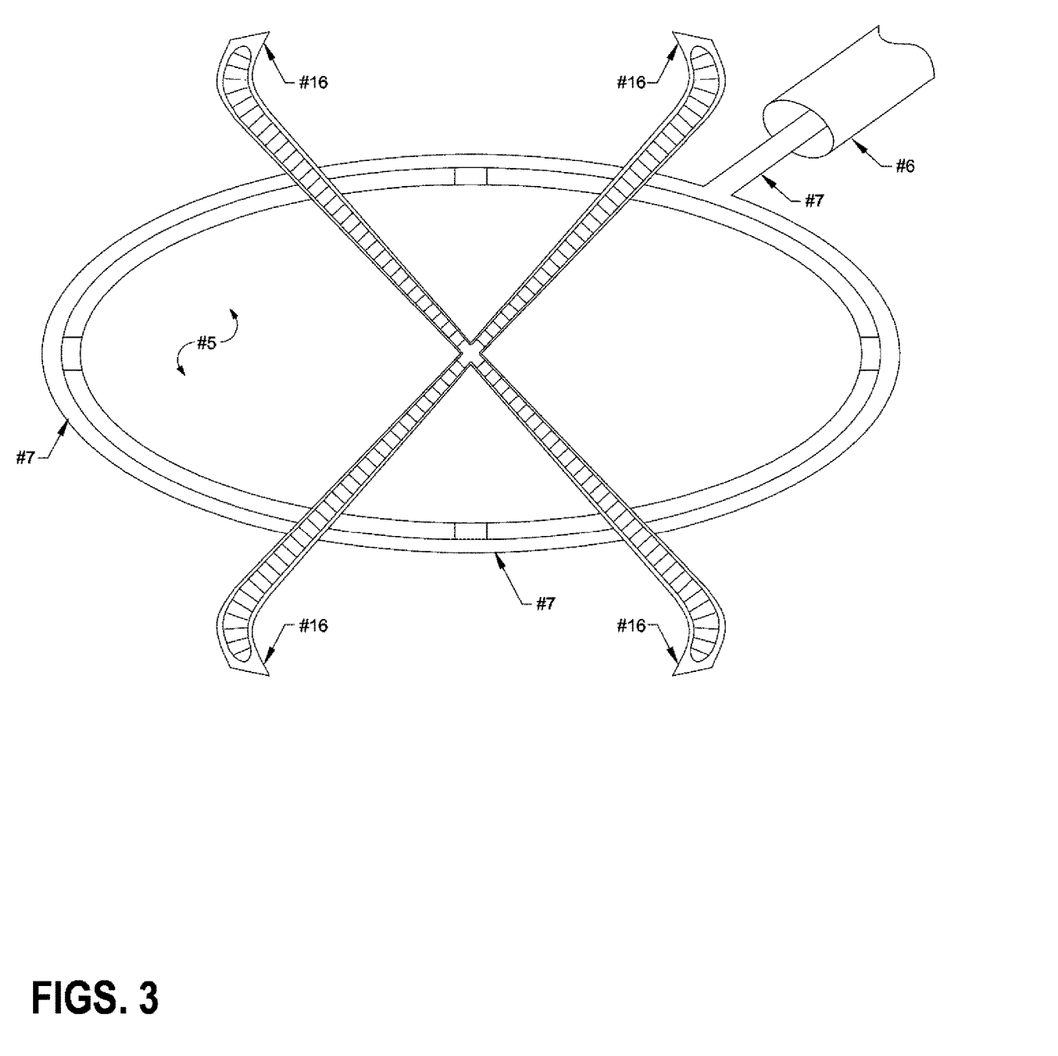
FIG. 3 is a below perspective view of the engulfing bag or engulfing sheet portion of the present invention. In this particular configuration, optional guiding tracks are included on the posterior surface of the engulfing sheet or engulfing bag. The engulfing bag or engulfing sheet is presented in a round shape in this representation, and is attached to the removable deployment tube and collapsible stabilizing harness.

As shown in FIG. 3, the opposite surface of the engulfing sheet or engulfing bag (#15) may in some configurations include guiding tracks (#16) in order to interface with gears that may be present on the ring harness. These guiding tracks may vary in size and shape in order to interface appropriately with different configurations of the size and shape of the engulfing sheet or engulfing bag. It may also be necessary for these guiding tracks to be larger than the engulfing sheet or engulfing bag itself, as they may in some configurations be used to exteriorize the mouth of the bag from the patient's body cavities prior to exteriorizing the mouth of the engulfing sheet or engulfing bag itself. The deployment tube (#6) is also show in FIG. 3. as it may serve to keep a small diameter to allow the engulfing sheet or engulfing bag, as well as the collapsible stabilizing harness (#7) to enter the patient's body, in order to engulf the tissue mass to be removed. The collapsible stabilizing harness may be flexible to enter through a small diameter and then expand to accommodate large tissue mass volumes. The collapsible stabilizing harness may constitute a full ring around the engulfing sheet or engulfing bag, or may border only a portion of the engulfing sheet or engulfing bag in other configurations. In this configuration the collapsible stabilizing harness is shown completely deployed (not collapsed) to illustrated that some degree of collapse will be necessary to fit the collapsible stabilizing harness into the much smaller diameter deployment tube. In the configuration shown in this figure the collapsible stabilizing harness is represented as a fully bordering the entire engulfing sheet or engulfing bag. In other configurations, the collapsible stabilizing harness may border only a portion of the engulfing sheet or engulfing bag. In this configuration the collapsible stabilizing harness is shown completely engaged to illustrated that some degree of collapse will be necessary to fit the collapsible stabilizing harness into the much smaller diameter deployment tube.

Figure 4:
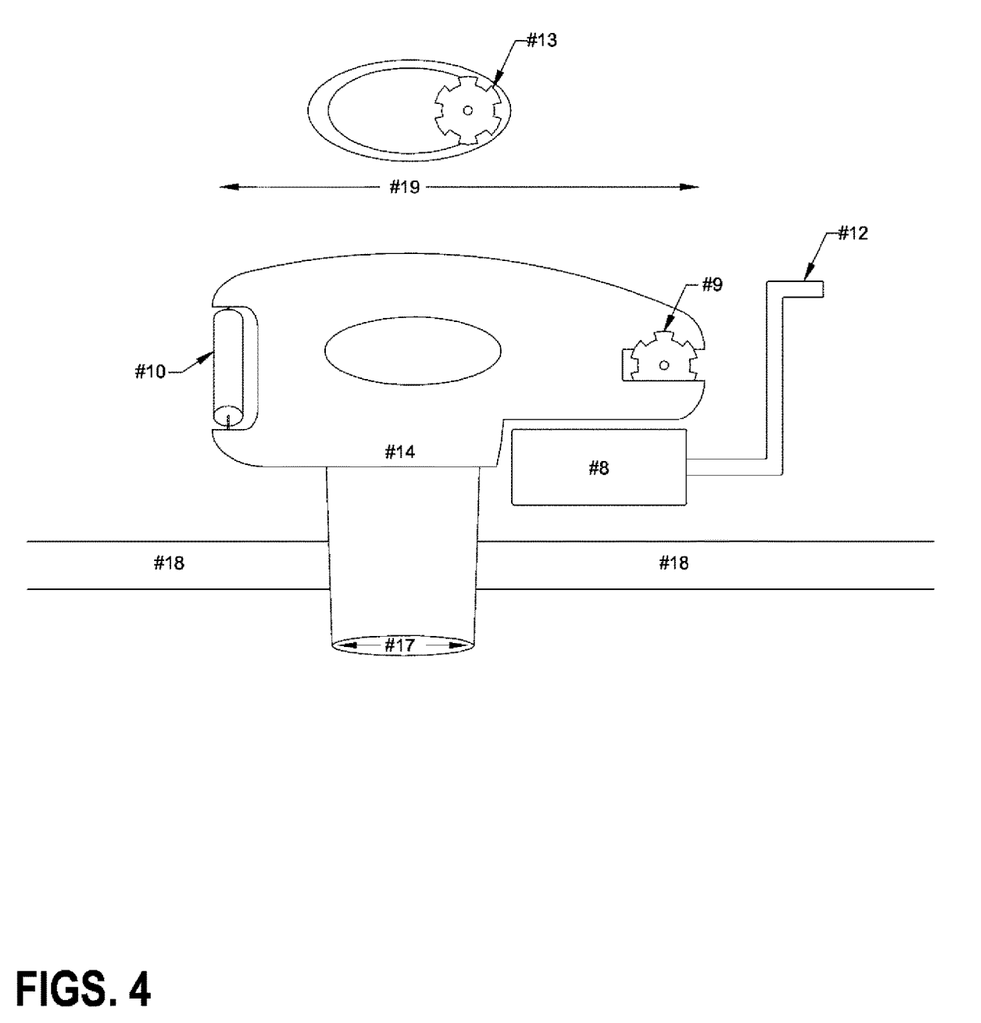
FIG. 4 is a side perspective of the ring harness of the device. This illustration shows the ring with accompanying gears and rolling pins, as well as an optional second interfacing inner ring of the harness. It is understood that variations of this device may have some or non of these components.

As illustrated in FIG. 4., The device includes a ring harness (#14) through which the tissue is transported to, and forced into a diameter smaller than the inside diameter of the ring harness. The inside diameter of the ring harness (#17) should be small enough diameter to facilitate the procedure being performed through a much smaller incision than the largest diameter of the tissue mass being removed. This would include, but not be limited to, removing large masses through 10 mm to 30 mm diameters as is commonly used in many aspects of endoscopic surgery. The ring harness is then placed into the incision, which will preferably be the size of the internal ring of the ring harness, with the outside diameter of the ring harness (#19) being larger than the incision, preventing it from falling into the incision. The inside diameter of the ring harness should be smaller than the incision, so that it can fit into the incision. The bottom of the ring harness, the portion inside the patient, should meet the tissue mass inside the engulfing sheet or engulfing bag a small distance inside the patient's body, as to avoid catching the internal walls of the patient's body in the compression of the device. The device also includes a mechanical device on the ring harness (#8) including one or a series of gears (#9) or rolling pins (#10) to pull the engulfing sheet or engulfing bag through the harness with sufficient force to reduce the entrapped tissue to the diameter of the harness. This mechanical device may be of an electronic type or may be powered by a manual crank type of system to be powered by the user of the device. A configuration including a manual "crank" (#12) is pictured in this illustration. The described gears or rolling pins may be on the outside of the bag only, or duplicated on the inside of the bag as well by doubling the ring harness with a second interfacing inner ring harness (#13). The gears or rolling pins of the mechanical device may pull the bag through the ring harness using guiding tracks, if present, or may simply articulate with the surface of the engulfing bag or engulfing sheet either by interlocking with the particular material of the layers of the bag or by using sheer force. In the case of a duplicated set of gears or rolling pins on a second internal interfacing ring the same traction could be accomplished by compression between the two sets of gears or rolling pins. The ring harness pictured in this particular illustration extends into the patient's body cavity and does not require an additional device, either inside or outside the patient, in order to prevent the tissue mass being removed from coming into contact with the internal or external surfaces of the patient. The wall of the patient's body cavity is also shown in this figure (#18) In other configurations of this device, the ring harness may be of a different size and shape in order to work with other devices which may have been used to initially enter the patient's body or may be instruments customary to performing surgery on this area of the body. In some configurations the ring harness may be placed in conjunction with these devices. In the configuration pictured the ring harness, which may be made of metal, plastic, Kevlar, or other materials, has sufficient size to avoid the direct contact of the engulfing sheet or engulfing bag with the internal or external surfaces of the patient's body. Other configurations may not require such large dimensions because of the interface with existing devices such as trochars.

Figure 5:
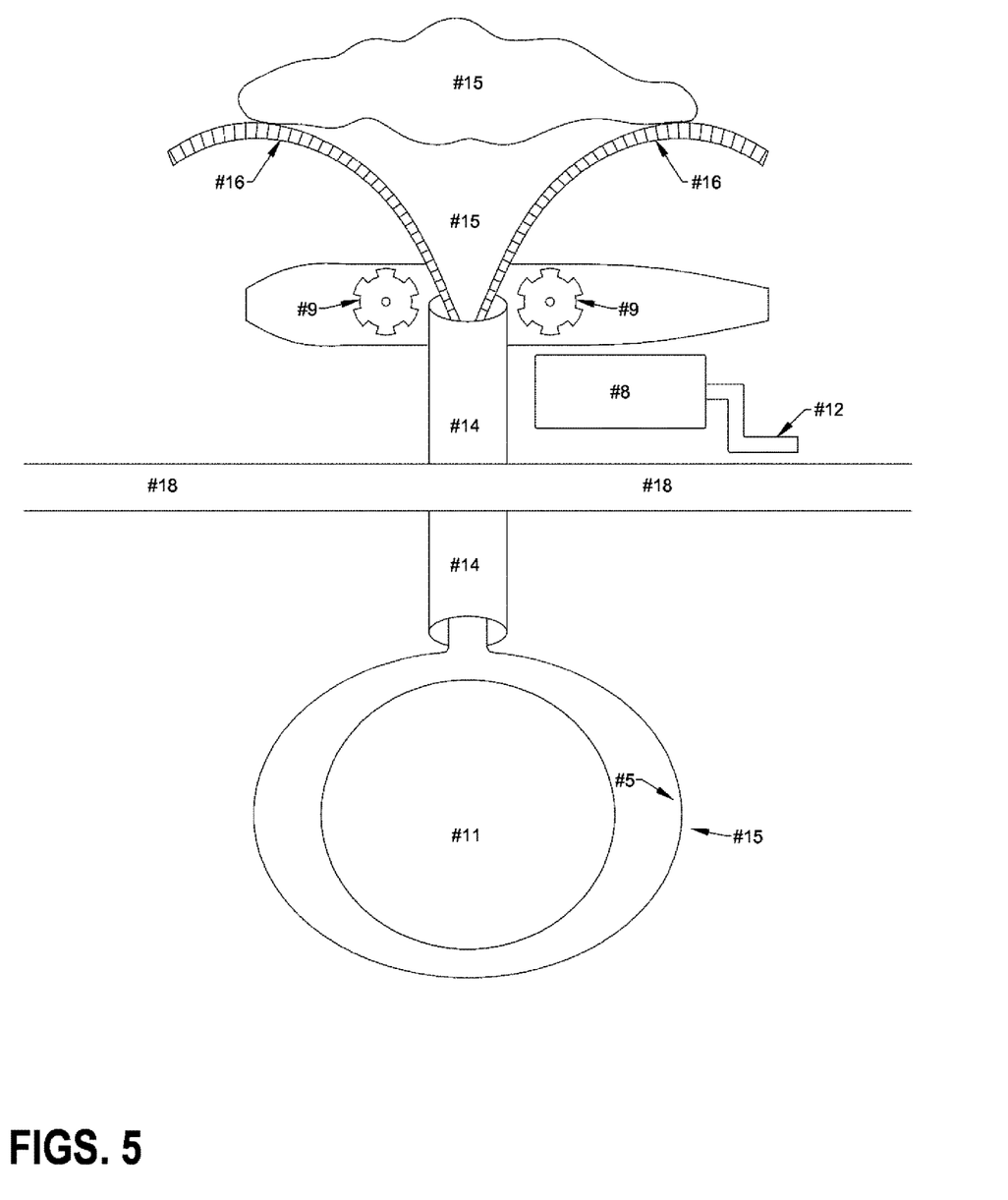
FIG. 5 is an illustration of the function of the device, with representations of where portions of the device could sit within a patient when removing a tissue mass. The configuration shown in this illustration does not contain a second inner ring for the ring harness, a deployment tube or collapsible stabilizing harness. Gears are depicted on the ring harness and guiding tracks are illustrated on the posterior surface of the engulfing sheet or engulfing bag in this configuration.

The functionality of the device is demonstrated in FIG. 5., where is it illustrated that the tissue mass (#11) is already within the engulfing sheet or engulfing bag, and the mouth of the bag has been exteriorized. As it is illustrated the mechanical device has not yet forced the remainder of the engulfing sheet or engulfing bag out of the abdominal cavity through the ring harness, but the mouth of the engulfing sheet or engulfing bag has been pulled through, along with the deployment tube and collapsible stabilizing harness which are illustrated in this configuration. It is illustrated that the tissue mass, as it is forced out within the engulfing sheet or engulfing bag, would be forced, using mechanical energy to fit to the internal diameter of the ring harness. The integral concept of the device is that without the use of morcellation this process will remove large tissue masses without large incisions, effectively making the surgical procedure more minimally invasive.

Use

The purpose of the device is to remove a large mass from the patient's body through a small incision without morcellating the mass. Therefore, in use, an incision in the body must first be made, or the device may be used through a natural orifice such as the vagina, or anus. Following this the mass, if connected to the patient through any means, must be first disconnected from the patient. This can be performed by any method reasonable to the field and anatomic location of the tissue mass. The ring harness is then placed into the incision, which will preferably be the size of the ring harness, with the outside diameter of the ring harness being larger than the incision, preventing it from falling into the incision. The inside diameter of the ring harness should be smaller than the incision, so that it can fit into the incision. The bottom of the ring harness, the portion inside the patient, should meet the tissue mass inside the engulfing sheet or engulfing bag a small distance inside the patient's body, as to avoid catching the internal walls of the patient's body in the compression of the device. The user would then place the engulfing sheet or engulfing bag inside the patient's body cavity through the ring harness, or in some configurations the engulfing sheet or engulfing bag could be placed in the patient's body before placement of the ring harness. The introduction of the engulfing sheet or engulfing bag into the patient's body may be using a deployment tube and a collapsible stabilizing harness, or either of these devices or neither. The tissue mass to be removed is then placed inside the engulfing sheet or engulfing bag, and the mouth of the engulfing sheet or engulfing bag is then exteriorized through the ring harness. The mechanical device described then pulls the engulfing sheet or engulfing bag the rest of the way out of the patient, with or without the use of guiding tracks. This can be done using electrical or manual energy using gears, rolling pins, other means. By the process of pulling the tissue mass through the small diameter ring harness, the mass will be reduced to the internal diameter of the ring harness, minimizing the size of the incision or hole needed to remove the tissue mass. In this way very large masses can be removed through very small incisions or holes without the need for morcellation.

The engulfing sheet or engulfing bag for removing the tissue may include, a series of guiding tracks and may comprise of one or more layers of largely impenetrable materials. These materials may include single, alternating or repeating layers of metal, plastic, rubber, Kevlar, or other materials in order to achieve the goals of flexibility, strength, and to a reasonable degree having the characteristic of being impenetrable. These materials may be fashioned into sheets of mesh, chain like sheets, three-dimensional woven sheets, sheets of connected plates, or other configurations to achieve the goals of flexibility, strength, and to a reasonable degree having the characteristic of being impenetrable. This engulfing sheet or engulfing bag may be of any shape or size, and may be designed to collaborate with a collapsible stabilizing harness, and/or a deployment tube in order to best be utilized to engulf objects with the patient's body. The engulfing sheet or engulfing bag may also contain guiding tracks which may be used to assist in removing the bag from the patient's body, possible interfacing with gears or rolling pins, in another configuration gears or rolling pins may simple interface with the surface of the bag, especially in configurations utilizing a chain-like or mesh-like bottom surface of the engulfing sheet or engulfing bag. The engulfing sheet or engulfing bag is used for the purpose of removing a large tissue mass from the patient's body by compressing the mass to a small diameter through a ring harness.

The ring harness device, made of hard material such as metal, diamond, plastic, Kevlar, stone, or another material, and containing an internal ring, of small diameter which is to be placed inside the patient's body. The ring harness will also have an external outside larger diameter that will be designed to stay outside of the patient's body. The size of the ring harness device will depend on the area of the body being worked on, as the distance between the top exterior ring, outside the patient's body, and the smaller interior ring will need to traverse into the body cavity that the mass is being removed from, the inside diameter of the ring harness should be small enough diameter to facilitate the procedure being performed through a much smaller incision than the largest diameter of the tissue mass being removed, this would include, but not be limited to, removing large masses through 10 mm to 30 mm diameters as is commonly used in many aspects of endoscopic surgery. The device also includes a mechanical device on the ring harness, including one or a series of gears or rolling pins, to pull the engulfing sheet or engulfing bag through the harness with sufficient force to reduce the entrapped tissue to the diameter of the harness. This mechanical device, may be of an electronic type or may be powered by a manual crank type of system to be powered by the user of the device, the described gears or rolling pins bay be on the outside of the bag only, or duplicated on the inside of the bag as well by doubling the ring harness with a second interfacing inner ring harness. The gears or rolling pins of the mechanical device may pull the bag through the ring harness using guiding tracks, if present, or may simply articulate with the surface of the engulfing bag or engulfing sheet either by interlocking with the particular material of the layers of the bag or by using sheer force. In the case of a duplicated set of gears or rolling pins on a second internal interfacing ring the same traction could be accomplished by compression between the two sets of gears or rolling pins. The ring harness pictured in FIG. 5 extends into the patient's body cavity and does require an additional device, either inside or outside the patient, in order to prevent the tissue mass being removed from coming into contact with the internal or external surfaces of the patient. In other configurations of this device, the ring harness may be of a different size and shape in order to work with other devices which may have been used to initially enter the patient's body or may be instruments customary to performing surgery on this area of the body. In some configurations the ring harness may be placed in conjunction with these devices. In the configuration pictured the ring harness, which may be made of metal, plastic, Kevlar, or other materials, has sufficient size to avoid the direct contact of the engulfing sheet or engulfing bag with the internal or external surfaces of the patient's body. Other configurations may not require such large dimensions because of the interface with existing devices such as trocars.

The system utilized consists minimally of a largely impenetrable engulfing sheet or engulfing bag which is used to remove a tissue mass from a body cavity. The method includes engulfing the tissue mass within the engulfing sheet or engulfing bag, and then reducing the size of the tissue mass by pulling the tissue mass within the engulfing sheet or bag out of the body cavity through a smaller diameter rigid hole or ring, using either manual or electronic power, including the method and process for removing a tissue mass from inside the body of a patient, by engulfing the tissue mass with a largely impenetrable engulfing sheet or engulfing bag, and then reducing the size of the tissue mass by pulling it out through a smaller diameter rigid hole or ring, using either manual or electronic power, with or without the use of other devices.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A laparoscopic surgical method for removing a non-morcellated tissue mass from a body cavity comprising:
   a) making an incision in the body to create an opening into the body cavity;
   b) separating the tissue mass from any connection from the body in a manner such that the entirety of the tissue mass consists of a single, non-morcellated tissue mass;
   c) placing a surgical ring into the opening into the body cavity,
      wherein the surgical ring comprises a lower ring section which passes through the opening into the body cavity, an upper platform which is in communication with the lower ring section and resides above the external surface of the body, and a primary gear set which is located on the upper platform, and whereas
      said lower ring section comprises a tube with a distal and proximal end, wherein the outer diameter of the tube at the distal end of the lower ring section is configured to be smaller than the diameter of the opening into the body cavity, and the inner diameter of the tube at the distal end defines the base of a generally cylindrical passage;
      the lower surface of the upper platform, where the upper platform and lower body connect, has a diameter greater than the diameter of the opening into the body cavity, and wherein the cylindrical passage continues through the upper platform to an upper surface of the upper platform; and said primary gearset, comprising at least one gear positioned on the upper surface of the upper platform and in close proximity to an edge of the cylindrical passage, is orientated such that the gear can rotate to extract material from the cylindrical passage;

d) passing the distal end of a receptacle deployment tool from outside the body cavity, through the surgical ring, and into the body cavity, wherein the receptacle deployment tool has a generally tube-like structure and wherein a sheet-like receptacle is attached to a support harness;
  a. said support harness having a ring attached to the distal end of an elongated member, said elongated member configured to axially traverse along the interior of the tube of the deployment tool;
  b. said sheet-like receptacle having a series of tabs along the perimeter which are joined to the ring of the deployment tube; and
  c. said sheet-like receptacle having a set of guiding tracks positioned on a surface of the receptacle which extending beyond the perimeter of the receptacle;

e) deploying the receptacle into the body cavity;

f) placing the disconnected tissue mass into the receptacle;

g) exteriorizing the mouth of the receptacle through the cylindrical passage;

h) extruding the receptacle and tissue mass contained within, through the cylindrical passage by utilizing mechanical energy provided by the rotation of the gear set on the upper platform of the ring harness in communication with the guiding tracks.

2. The laparoscopic surgical method of claim 1 wherein the incision in the body is much smaller than the largest diameter of the non-morcellated tissue mass being removed.

3. The laparoscopic surgical method of claim 2 wherein the diameter of the non-morcellated tissue mass is between 10 mm and 30 mm.

4. A laparoscopic surgical method for removing a non-morcellated tissue mass from the body cavity through a natural orifice of the body comprising:

a) performing a surgical procedure, utilizing any variety of known methods commonly practiced, to separate the tissue mass from any connection from the body in a manner such that the entirety of the tissue mass consists of a single, non-morcellated tissue mass and continues to reside within the body cavity;

b) placing a surgical ring into the natural orifice into the body cavity,
  wherein the surgical ring comprises a lower ring section which passes through the natural orifice into the body cavity, an upper platform which is in communication with the lower ring section and resides above the external surface of the body, and a primary gear set which is located on the upper platform, and whereas
  said lower ring section comprises a tube with a distal and proximal end, wherein the outer diameter of the tube at the distal end of the lower ring section is configured to be smaller than the diameter of the natural orifice into the body cavity, and the inner diameter of the tube at the distal end defines the base of a generally cylindrical passage;
  the lower surface of the upper platform, where the upper platform and lower body connect, has a diameter greater than the diameter of the natural orifice of the body cavity, and wherein the cylindrical passage continues through the upper platform to an upper surface of the upper platform; and
  said primary gearset, comprising at least one gear positioned on the upper surface of the upper platform and in close proximity to an edge of the cylindrical passage, is orientated such that the gear can rotate to extract material from the cylindrical passage;

c) passing the distal end of a receptacle deployment tool from outside the body cavity, through the surgical ring, and into the body cavity, wherein the receptacle deployment tool has a generally tube-like structure and wherein a receptacle with a bag-like structure is attached to a support harness;
  a. said support harness having a ring attached to the distal end of an elongated member, said elongated member configured to axially traverse along the interior of the tube of the deployment tool;
  b. said receptacle includes a mouth defined by the opening of the receptacle and having a series of tabs along the perimeter of the mouth which are joined to the ring of the deployment tube; and
  c. said receptacle having a set of guiding tracks positioned on a external surface of the receptacle which extend beyond the mouth of the receptacle;

d) deploying the receptacle into the body cavity;

e) placing the disconnected tissue mass into interior cavity of the receptacle;

f) exteriorizing the mouth of the receptacle through the cylindrical passage;

g) extruding the receptacle and tissue mass contained within, through the cylindrical passage by utilizing mechanical energy provided by the rotation of the gear set on the upper platform of the ring harness in communication with the guiding tracks.

5. The laparoscopic surgical method of claim 4 wherein the incision in the body is much smaller than the largest diameter of the non-morcellated tissue mass being removed.

6. The laparoscopic surgical method of claim 5 wherein the diameter of the non-morcellated tissue mass is between 10 mm and 30 mm.

* * * * *